(12) United States Patent
Berry (10) Patent No.: US 11,723,694 B2
(45) Date of Patent: Aug. 15, 2023

(54) ADJUSTABLE SPINOUS PROCESS IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 17/219,824

(22) Filed: Mar. 31, 2021

(65) Prior Publication Data

US 2022/0323119 A1 Oct. 13, 2022

(51) Int. Cl.
*A61B 17/70* (2006.01)

(52) U.S. Cl.
CPC ...... *A61B 17/7067* (2013.01); *A61B 17/7053* (2013.01); *A61B 17/7065* (2013.01)

(58) Field of Classification Search
CPC ............ A61B 17/7067; A61B 17/7062; A61B 17/7053
See application file for complete search history.

(56) References Cited

U.S. PATENT DOCUMENTS

| | | | | |
|---|---|---|---|---|
| 6,302,889 | B1 * | 10/2001 | Keller | A61B 17/82 606/74 |
| 8,317,832 | B2 | 11/2012 | Carls et al. | |
| 2002/0133155 | A1 * | 9/2002 | Ferree | A61B 17/7031 606/264 |
| 2007/0299445 | A1 * | 12/2007 | Shadduck | A61B 17/7011 606/100 |
| 2009/0105761 | A1 * | 4/2009 | Robie | A61B 90/06 606/86 A |
| 2009/0105820 | A1 * | 4/2009 | Jackson | A61B 17/7004 606/264 |
| 2009/0292317 | A1 * | 11/2009 | Belliard | A61B 17/7053 606/279 |

FOREIGN PATENT DOCUMENTS

EP 2138122 A1 * 12/2009 ......... A61B 17/7022

* cited by examiner

*Primary Examiner* — Julianna N Harvey
(74) *Attorney, Agent, or Firm* — McCarter & English, LLP; James M. Smedley; Alex Korona (57) ABSTRACT

An adjustable spinous process implant configured with one or more flexible members that extend from the implant and are further attachable to anchors implanted in adjacent vertebrae. The adjustable spinous process implant comprises a spacer that is shaped to fit between two adjacent spinal processes. The flexible members extend from one or more points on the adjustable spinous process implant and attach the anchors to provide tension and stability to the overall implant construct. The anchors are configured with a tensioning mechanism that enables the flexible members to be tensioned within the anchor.

17 Claims, 10 Drawing Sheets

ADJUSTABLE SPINOUS PROCESS IMPLANT

FIELD OF INVENTION

The present invention relates to a spinal implant configured to be inserted between the spinous processes of two adjacent vertebrae. The present invention also relates to a system of anchors and flexible members attachable to the spinal implant and configured enhance the stability of the overall implant system.

BACKGROUND OF THE INVENTION

Spinous process implants can be implanted between the spinal processes of two adjacent vertebrae to help provide stability to the spine. In many cases, the spinous process implant functions as spacer, which is component of an overall construct that also includes cables, wires, and anchors that work collectively to provide stability to the spine and maintain the spinous process implant in the correct orientation and position. An important aspect of securing the spinous process implant involves setting and tightening the cables and anchors that are attached to the spinous process implant. The stability provided by the cables attaching to the spinous process implant can be improved by integrating the cables directly into the spinous process implant. Furthermore, the tightening of the cables integrated within the spinous process implant could be streamlined by integrating a means for tightening the cables either within the spinous process implant itself or as a part of the cables.

Therefore, there is a need in the art for a spinous process implant that is configured with integrated cables and a means for tightening those cables efficiently and effectively. These and other features and advantages of the present invention will be explained and will become obvious to one skilled in the art through the summary of the invention that follows.

SUMMARY OF THE INVENTION

Accordingly, it is an aspect of the present invention to provide an adjustable spinous process implant configured with one or more flexible members that extend from the implant and are further attachable to anchors implanted in adjacent vertebrae. The adjustable spinous process implant comprises a spacer that is shaped to fit between two adjacent spinal processes, with a central portion flanked by a left and right stabilizer. The flexible members extend from one or more points on each of the left and right stabilizers. The distal ends of each flexible member attach to one of the anchors to provide tension and stability to the overall implant construct. In some embodiments, one or more of the flexible members are configured to loop around a spinal process of an adjacent vertebra to more securely position the implant. The anchors implanted into the vertebrae adjacent to where the implant is inserted and are configured with a tensioning mechanism that enables the flexible members to be tensioned within the anchor.

According to an embodiment of the present invention, an adjustable spinous process implant comprises a spacer and one or flexible member distal ends extending from the spacer.

According to an embodiment of the present invention, the adjustable spinous process implant further comprises one or more flexible members.

According to an embodiment of the present invention, each of the flexible members passes continuously through the spacer from one of the flexible member distal ends to another of the flexible member distal ends.

According to an embodiment of the present invention, each of the flexible member distal ends forms a terminal segment of one of the flexible members.

According to an embodiment of the present invention, the adjustable spinous process implant further comprises one or more loop portions formed from one or more of the one or more flexible members.

According to an embodiment of the present invention, the spacer is formed with a central body connecting between a right stabilizer and a left stabilizer.

According to an embodiment of the present invention, the adjustable spinous process implant further comprises one or more turnbuckles.

According to an embodiment of the present invention, at least one of the turnbuckles is attached to one of the flexible member distal ends.

According to an embodiment of the present invention, a turnbuckle is configured in the spacer.

According to an embodiment of the present invention, the adjustable spinous process implant further comprises one or more anchors, each of the anchors configured to attach to one of the flexible member distal ends.

According to an embodiment of the present invention, each of the anchors is configured with a tensioning mechanism.

According to an embodiment of the present invention, an adjustable spinous process implant comprises a spacer, one or flexible member distal ends extending from the spacer, and one or more turnbuckles.

According to an embodiment of the present invention, at least one of the one or more turnbuckles is positioned between the spacer and an endpoint of one of the flexible member distal ends.

According to an embodiment of the present invention, an adjustable spinous process implant comprises a spacer, one or flexible member distal ends extending from the spacer; and one or more anchors, each of the anchors configured to attach to one of the flexible member distal ends.

According to an embodiment of the present invention, one of the turnbuckles is configured in a central body portion of the spacer.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

DETAILED DESCRIPTION

In the Summary above and in this Detailed Description, and the claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally. It should be noted that the features illustrated in the drawings are not necessarily drawn to scale and descriptions of well-known components and techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

In accordance with embodiments of the present invention, the adjustable spinous process implant disclosed herein is configured to be implanted between two adjacent vertebrae. The implant provides decompression of the vertebral disc and the adjacent nerve roots, while allowing the adjacent vertebral bodes to still move. The implant also provides stability by creating tension to help restrict motion to more closely mimic the natural motion of the spine. This is particularly important due to the fact that often the posterior longitudinal ligament is removed in order to implant a spinous process spacer. Removing the posterior longitudinal ligament removes the tension band of the natural spine.

First Exemplary Embodiment

FIGS. 1-5 depict a first preferred embodiment of an adjustable spinous process implant. In the first preferred embodiment the adjustable spinous process implant 10 comprises a spacer 20, two anchors 30, 40 and a flexible member 50. In the first preferred embodiment, the spacer 20 is an H-shaped component formed by a central body 22 that connects between a right stabilizer 24 and a left stabilizer 26.

Figure 1:
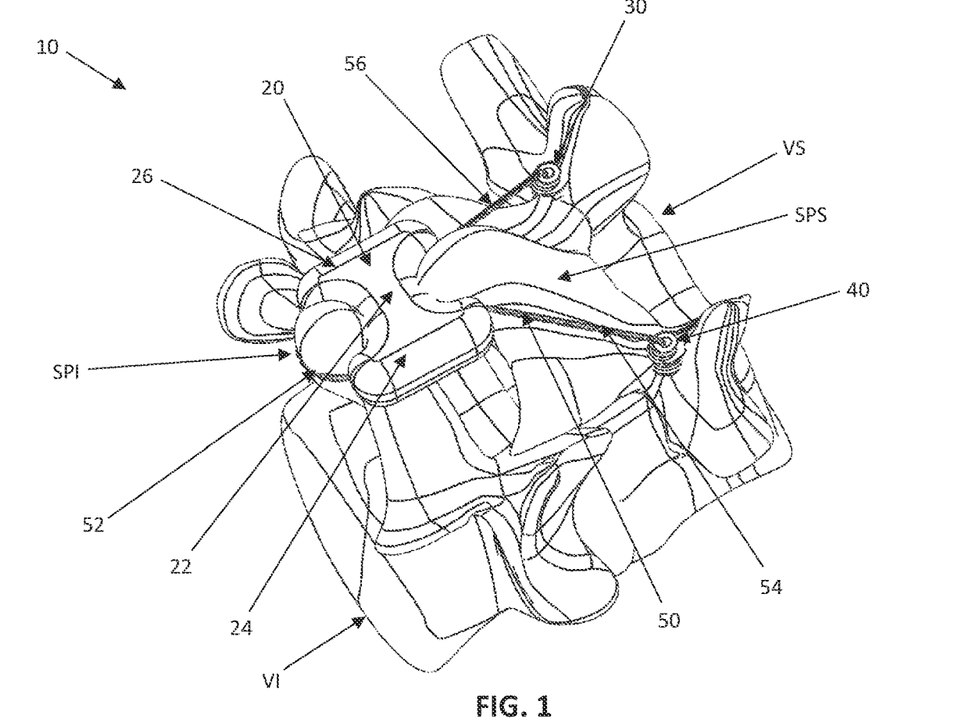
FIG. 1 is an isometric view of a first embodiment of an adjustable spinous process implant inserted between two adjacent vertebrae.
Figure 2:
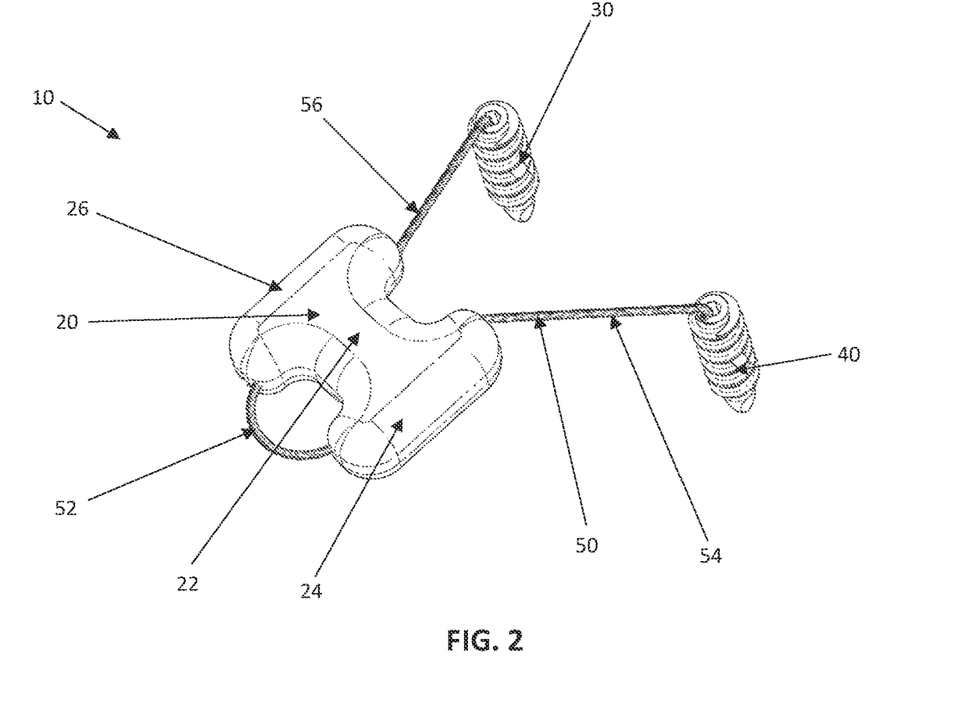
FIG. 2 is an isometric view of a first embodiment of an adjustable spinous process implant.
Figure 3:
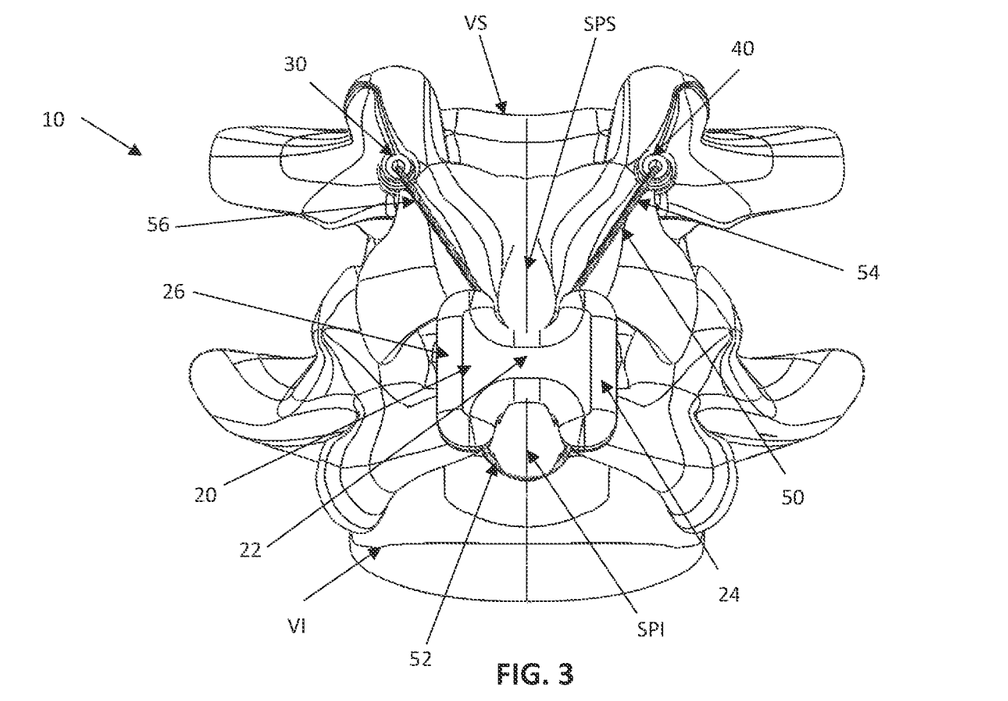
FIG. 3 is a posterior view of a first embodiment of an adjustable spinous process implant inserted between two adjacent vertebrae.
Figure 4:
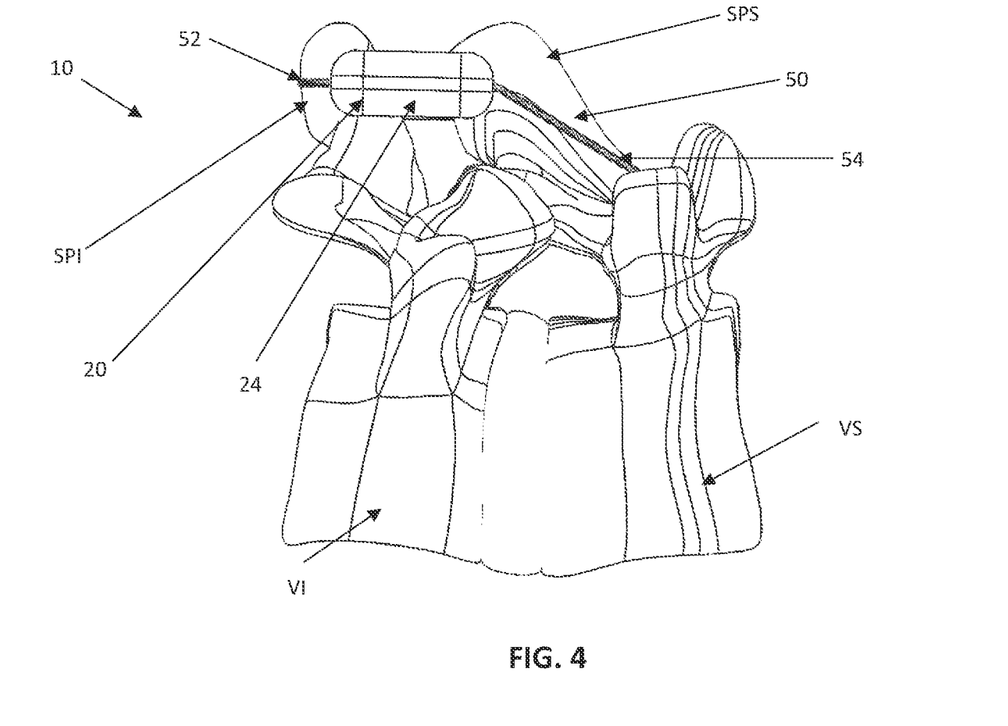
FIG. 4 is a lateral view of a first embodiment of an adjustable spinous process implant inserted between two adjacent vertebrae.
Figure 5:
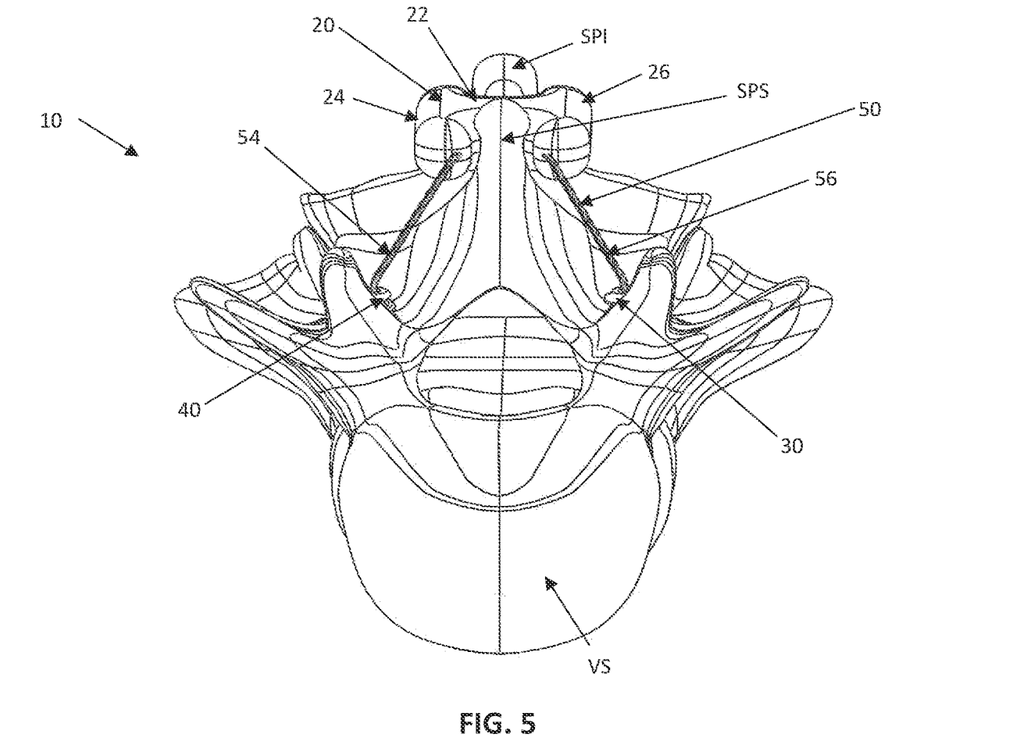
FIG. 5 is a superior view of a first embodiment of an adjustable spinous process implant inserted between two adjacent vertebrae.

As shown by at least FIG. 1 and FIG. 3, the central body 22 of the spacer 20 is designed to fit between the Inferior Spinous Process SPI and the Superior Spinous Process SPS of two adjacent vertebrae, where the Inferior Spinous Process SPI is on the Inferior Vertebra VI of the two adjacent vertebrae and the Superior Spinous Process SPS is on the Superior Vertebra VS of the two adjacent vertebrae. The right stabilizer 24 and left stabilizer 26 are configured to steady the spacer 20 between the Inferior Spinous Process SPI and the Superior Spinous Process SPS as the Inferior Vertebra VI and Superior Vertebra VS rotate with respect to one another. Additionally, the right stabilizer 24 and left stabilizer 26 cooperate to restrict the motion of the Inferior Spinous Process SPI and the Superior Spinous Process SPS relative to one another. As shown by at least FIGS. 3-5, both the right stabilizer 24 and left stabilizer 26 have portions that extend above and below the central body 22 of the spacer 20 to define a groove along both the lower and upper portions of the central body 22 that cradles the Inferior Spinous Process SPI and the Superior Spinous Process SPS, respectively. In the preferred embodiment, the spacer 20 may be made from flexible material such as a visco elastic polymer, or more rigid material such as polyether ether ketone (PEEK) or titanium. One of ordinary skill in the art would appreciate that there are numerous suitable and advantageous configurations for a spacer, including relative dimensions, size, and shapes, as well as different construction materials, depending on the intended use application, and embodiments of the present invention are contemplated for use with any such spacer configuration.

The first preferred embodiment of the adjustable spinous process implant 10 is further configured with a flexible member 50 that runs continuously through the spacer 20. The flexible member 50 may be one or more separate wires or cables integrated with or attached to the spacer 20. For example, each of the distal ends or loop(s) of the flexible member may be a separate wire or cable, with the separate wires or cables collectively comprising the flexible member. Furthermore, the wire(s) or cable(s) forming the flexible member 50, may pass straight through the stabilizers 24, 26 of the spacer 20, cross over in the central body 22, a combination thereof, or take any other path through the spacer 20 as necessary. In the various embodiments of the adjustable spinous implant 10, the distal ends and loop(s) of the flexible member 50 extend or protrude from various points along the spacer 20 in the given embodiment of the adjustable spinous implant 10. In some alternate embodiments of the flexible member 50, the flexible member does not run continuously through the spacer 20 and instead each distal end or loop, as described herein, is a separate component of the overall flexible member 50 that extends from a point on the spacer 20. In the first preferred embodiment, a right distal end 54 of the flexible member 50 protrudes from a superior portion of the right stabilizer 24 of the spacer 20 and connects to a right anchor 40. Correspondingly, a left distal end 56 of the flexible member 50 protrudes from a superior portion of the left stabilizer 26 of the spacer 20 and connects to a left anchor 30. Additionally, a loop portion 52 of the flexible member 50 protrudes from inferior portions of the right stabilizer 24 and left stabilizer 26 of the spacer 20. In the first preferred embodiment, the loop portion 52 is configured to loop around an inferior edge of the Inferior Spinous Process SPI. In the first preferred embodiment, the flexible member 50 can be manufactured from any suitable material, including but not limited to, steel cable, polyethylene fibers, and suture wire.

In the first preferred embodiment, the left anchor 30 and right anchor 40 each seat into the pedicle of the Superior Vertebrae VS. The proximal portion of the left anchor 30 attaches to the left distal end 56 of the flexible member 50 and the proximal portion of the right anchor 40 attaches to the right distal end 54 of the flexible member 50. In the first preferred embodiment, the anchors 30, 40 have a means by which the flexible member 50 can be tensioned within them. This enables a physician to tighten the flexible member 50 by drawing the distal ends 54, 56 into the respective anchors 30, 40 thereby tightening the loop portion 52 around the Inferior Spinous Process SPI. The tightening of the various elements of the flexible member 50, collectively pull the vertebral bodies VI, VS towards one another, while also placing the spacer 20 under compression from the two Spinous Processes SPI, SPS. In the first preferred embodiment, the tensioning method can be a secondary screw mechanism within each of the anchors 30, 40 which pulls the distal ends 54, 56 of the flexible member 50 distally along each anchor 30, 40. Alternatively, the tensioning method can be similar to suture anchors whereby the distal ends 54, 56 of the flexible member 50 are looped inside of the respective anchor 30, 40 and the distal ends 54, 56 of the flexible member 50 can be pulled tight and tied off at the desired tightness. One of ordinary skill in the art would appreciate that there are numerous suitable and advantageous configurations for an anchor and a tensioning method therefor, and embodiments of the present invention are contemplated for use with any such anchor configuration and tensioning method.

Second Exemplary Embodiment

FIGS. 6-10 depict a second preferred embodiment of an adjustable spinous process implant. In the second preferred embodiment the adjustable spinous process implant 110 comprises a spacer 120, four anchors 130, 140, 170, 180 and a flexible member 150. In the second preferred embodiment, the spacer 120 is an H-shaped component formed by a central body 122 that connects between a right stabilizer 124 and a left stabilizer 126.

Figure 6:
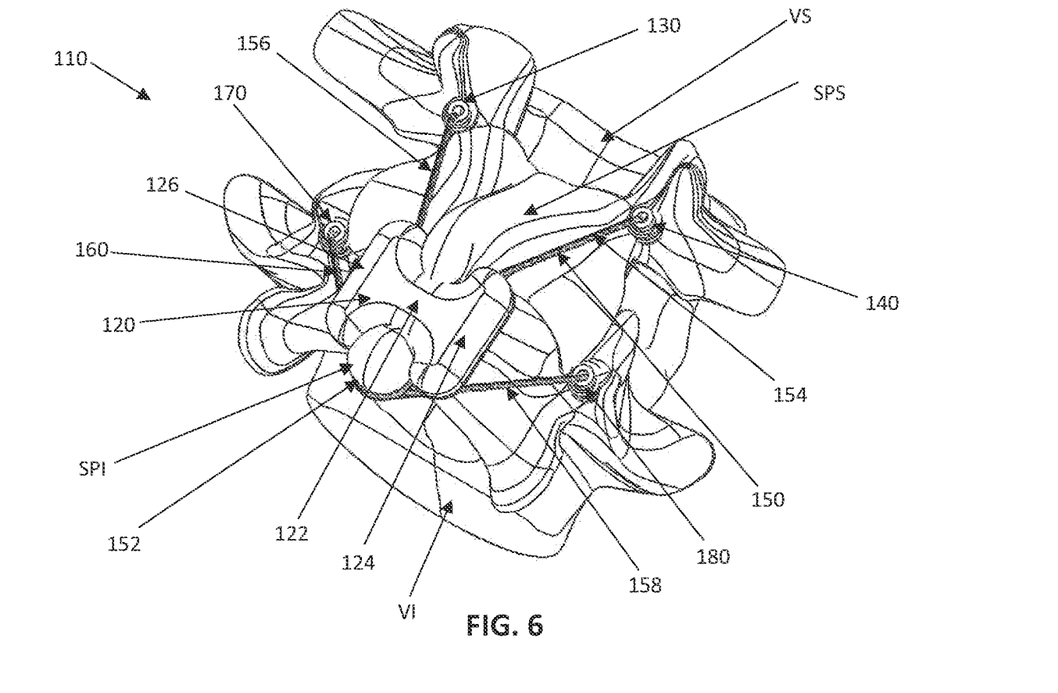
FIG. 6 is an isometric view of a second embodiment of an adjustable spinous process implant inserted between two adjacent vertebrae.
Figure 7:
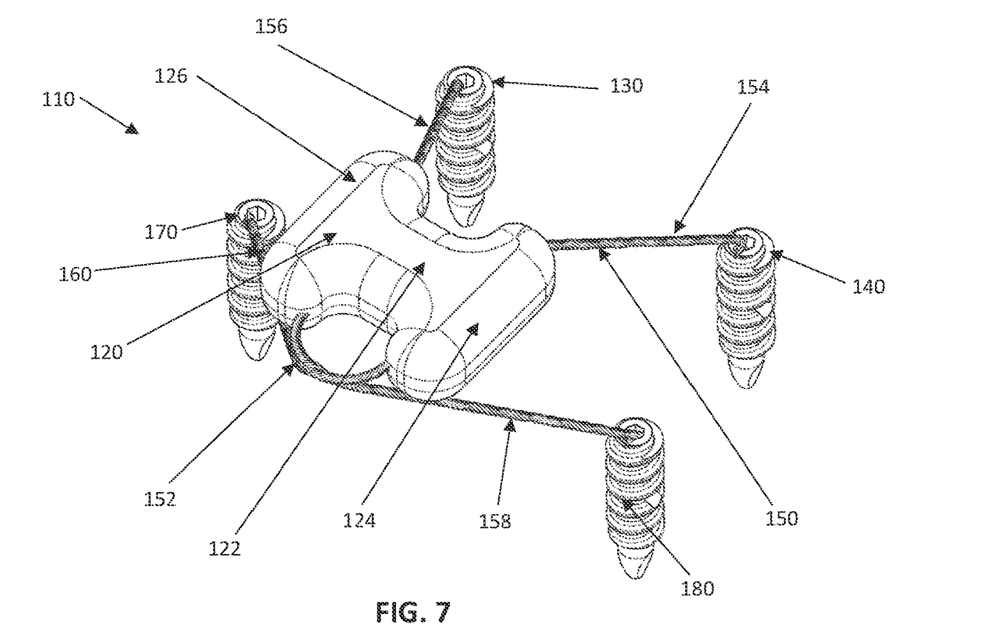
FIG. 7 is an isometric view of a second embodiment of an adjustable spinous process implant.
Figure 8:
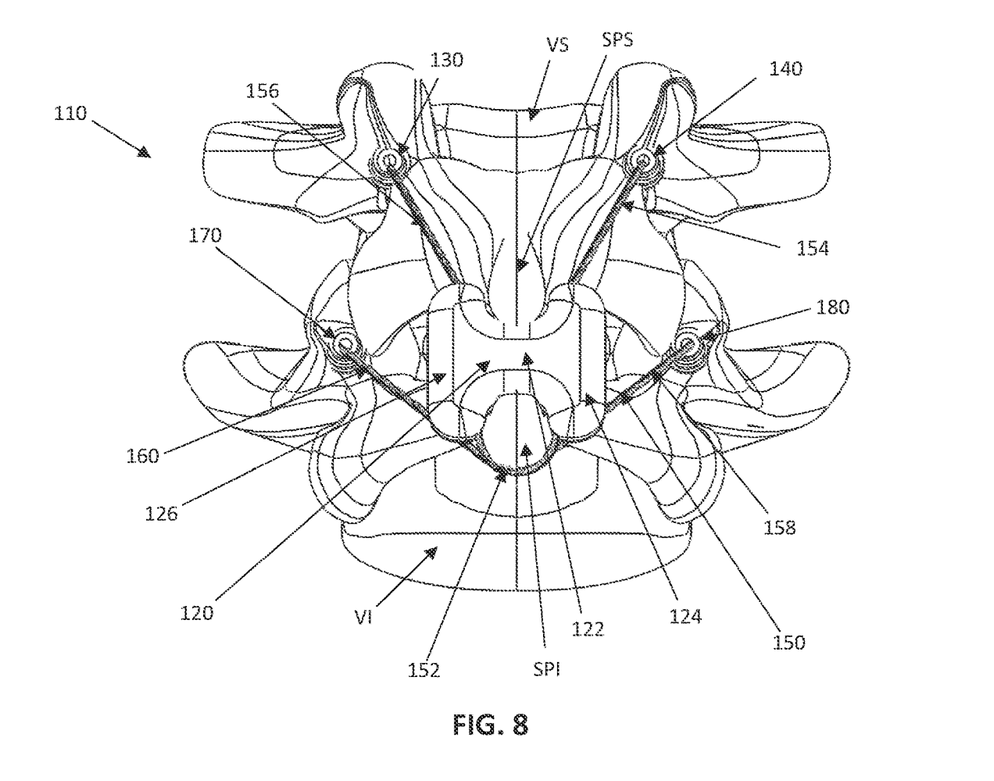
FIG. 8 is a posterior view of a second embodiment of an adjustable spinous process implant inserted between two adjacent vertebrae.
Figure 9:
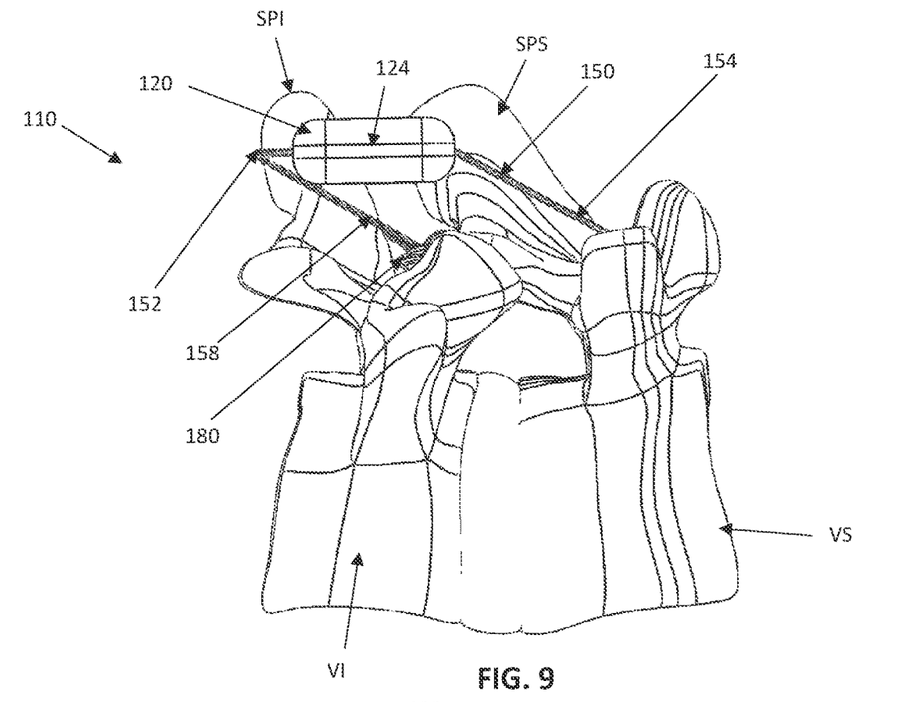
FIG. 9 is a lateral view of a second embodiment of an adjustable spinous process implant inserted between two adjacent vertebrae.
Figure 10:
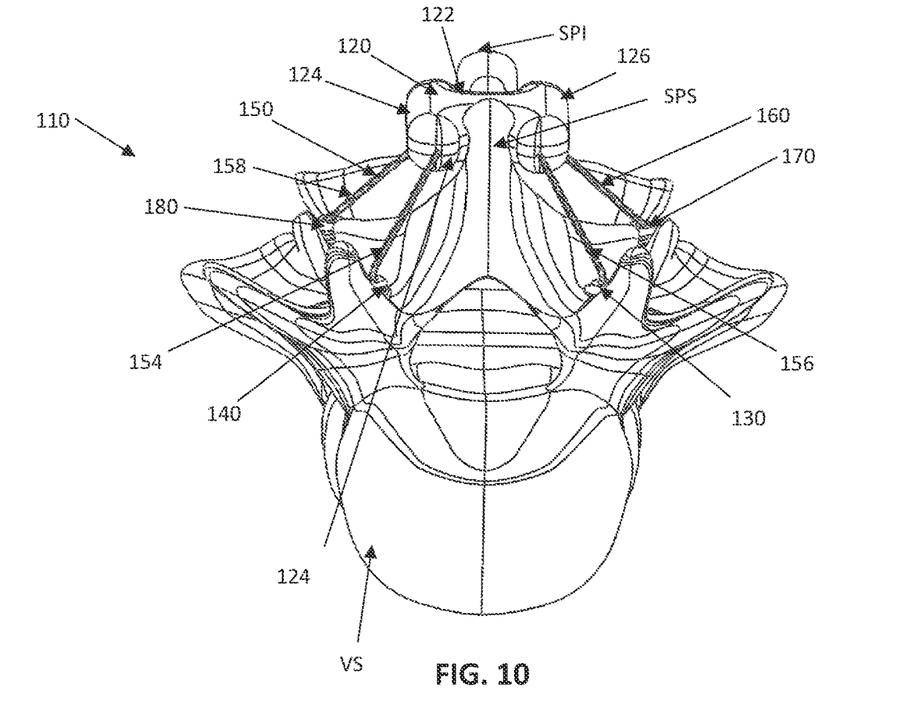
FIG. 10 is a superior view of a second embodiment of an adjustable spinous process implant inserted between two adjacent vertebrae.

As shown by at least FIG. 6 and FIG. 8, the central body 122 of the spacer 120 is designed to fit between the Inferior Spinous Process SPI and the Superior Spinous Process SPS of two adjacent vertebrae, where the Inferior Spinous Process SPI is on the Inferior Vertebra VI of the two vertebrae and the Superior Spinous Process SPS is on the Superior Vertebra VS of the two vertebrae. The right stabilizer 124 and left stabilizer 126 are configured to steady the spacer 120 between the Inferior Spinous Process SPI and the Superior Spinous Process SPS as the Inferior Vertebra VI and Superior Vertebra VS rotate with respect to one another. Additionally, the right stabilizer 124 and left stabilizer 126 cooperate to restrict the motion of the Inferior Spinous Process SPI and the Superior Spinous Process SPS relative to one another. As shown by at least FIGS. 8-10, both the right stabilizer 124 and left stabilizer 126 have portions that extend above and below the central body 122 of the spacer 120 to define a groove along both the lower and upper portions of the central body 122 that cradles the Inferior Spinous Process SPI and the Superior Spinous Process SPS, respectively. In the preferred embodiment, the spacer 120 may be made from flexible material such as a visco elastic polymer, or more rigid material such as polyether ether ketone (PEEK) or titanium. One of ordinary skill in the art would appreciate that there are numerous suitable and advantageous configurations for a spacer, including relative dimensions, size, and shapes, as well as different construction materials, depending on the intended use application, and embodiments of the present invention are contemplated for use with any such spacer configuration.

The second preferred embodiment of the adjustable spinous process implant 110 is further configured with a flexible member 150 that runs continuously through the spacer 120. The flexible member 150 may be one or more separate wires or cables integrated with or attached to the spacer 120. For example, each of the distal ends or loop(s) of the flexible member may be a separate wire or cable, with the separate wires or cables collectively comprising the flexible member. Furthermore, the wire(s) or cable(s) forming the flexible member 150, may pass straight through the stabilizers 124, 126 of the spacer 120, cross over in the central body 122, a combination thereof, or take any other path through the spacer 120 as necessary. In the various embodiments of the adjustable spinous implant 110, the distal ends and loop(s) of the flexible member 150 extend or protrude from various points along the spacer 120 in the given embodiment of the adjustable spinous implant 110. In some alternate embodiments of the flexible member 150, the flexible member does not run continuously through the spacer 120 and instead each distal end or loop, as described herein, is a separate component of the overall flexible member 150 that extends from a point on the spacer 120. In the second preferred embodiment, a right superior distal end 154 of the flexible member 150 protrudes from a superior portion of the right stabilizer 124 of the spacer 120 and connects to a right superior anchor 140. Correspondingly, a left superior distal end 156 of the flexible member 150 protrudes from a superior portion of the left stabilizer 126 of the spacer 120 and connects to a left superior anchor 130. Additionally, a right inferior distal end 158 of the flexible member 150 protrudes from an inferior portion of the left stabilizer 126 of the spacer 120 and crosses over with a left inferior distal end 160 of the flexible member 150 that protrudes from an inferior portion of the right stabilizer 124 of the spacer 120 to form a loop portion 152 in the flexible member 150. In the second preferred embodiment, the loop portion 152 is configured to loop around the inferior edge of the Inferior Spinous Process SPI. The loop portion 152 is enabled because the right inferior distal end 158 of the flexible member 150 extends from the left stabilizer 126, loops around the inferior face of the Inferior Spinous Process SPI, and then connects to the right inferior anchor 180.

Correspondingly, the loop portion 152 is further enabled because the left inferior distal end 160 extends from the right stabilizer 124, loops around the inferior face of the Inferior Spinous Process SPI, and then connects to the left inferior anchor 170. In the second preferred embodiment, the flexible member 150 can be manufactured from any suitable material, including but not limited to, steel cable, polyethylene fibers, and suture wire.

In the second preferred embodiment, the left superior anchor 130 and right superior anchor 140 seat into the pedicle of the Superior Vertebrae VS, while the left inferior anchor 170 and right inferior anchor 180 seat into the pedicle of the Inferior Vertebrae VI. The proximal portion of the left superior anchor 130 attaches to the left superior distal end 156 of the flexible member 150 and the proximal portion of the right superior anchor 140 attaches to the right superior distal end 154 of the flexible member 150. Correspondingly, the proximal portion of the left inferior anchor 170 attaches to the left inferior distal end 160 of the flexible member 150 and the proximal portion of the right inferior anchor 180 attaches to the right inferior distal end 158 of the flexible member 150.

In the second preferred embodiment, the anchors 130, 140, 170, 180 have means by which the flexible member 150 can be tensioned within them. This enables a physician to tighten the flexible member 150 by drawing the distal ends 154, 156, 158, 160 into the respective anchors 130, 140, 170, 180 thereby tightening the loop portion 152 around the Inferior Spinous Process SPI. The tightening of the various elements of the flexible member 150, collectively pull the vertebral bodies VI, VS towards one another, while also placing the spacer 120 under compression from the two Spinous Processes SPI, SPS. In the second preferred embodiment, the tensioning method can be a secondary screw mechanism within each of the anchors 130, 140, 170, 180 which pulls the distal ends 154, 156, 158, 160 of the flexible member 150 distally along each anchor 130, 140, 170, 180. Alternatively, the tensioning method can be similar to suture anchors whereby the distal ends 154, 156, 158, 160 of the flexible member 150 are looped inside of the respective anchors 130, 140, 170, 180 and the distal ends 154, 156, 158, 160 of the flexible member 150 can be pulled tight and tied off at the desired tightness. One of ordinary skill in the art would appreciate that there are numerous suitable and advantageous configurations for an anchor and a tensioning method therefor, and embodiments of the present invention are contemplated for use with any such anchor configuration and tensioning method.

Third Exemplary Embodiment

FIGS. 11-15 depict a third preferred embodiment of an adjustable spinous process implant. In the third preferred embodiment, the adjustable spinous process implant 210 comprises a spacer 220, four anchors 230, 240, 270, 280 and a flexible member 250. In the third preferred embodiment, the spacer 220 is an H-shaped component formed by a central body 222 that connects between a right stabilizer 224 and a left stabilizer 226.

Figure 11:
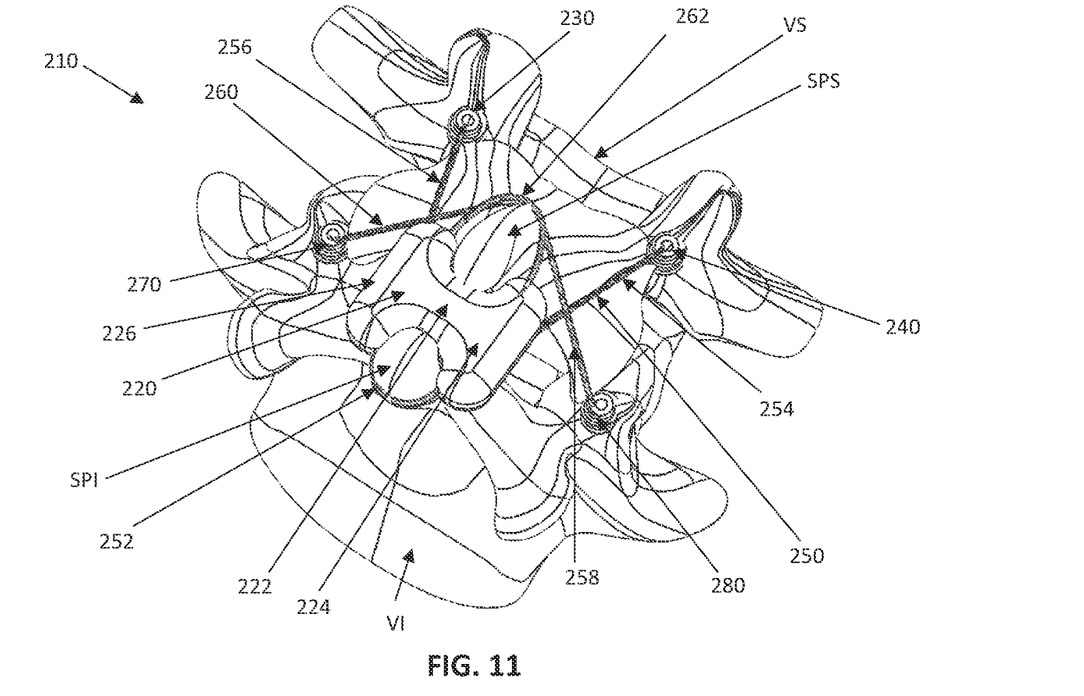
FIG. 11 is an isometric view of a third embodiment of an adjustable spinous process implant inserted between two adjacent vertebrae.
Figure 12:
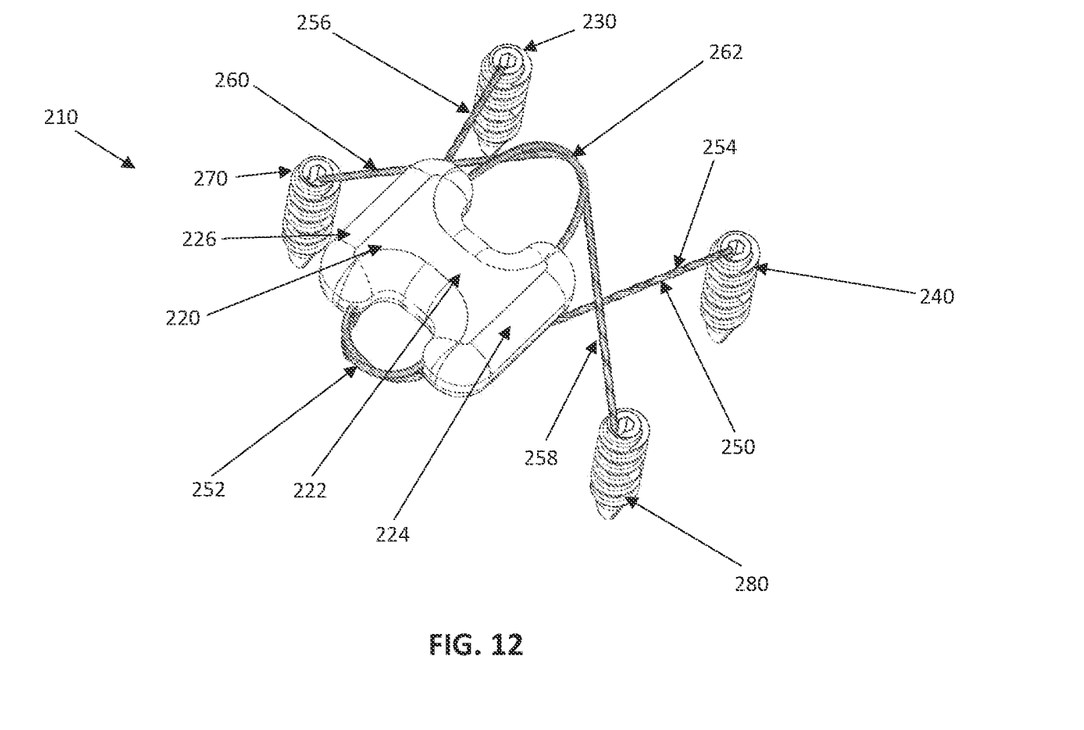
FIG. 12 is an isometric view of a third embodiment of an adjustable spinous process implant.
Figure 13:
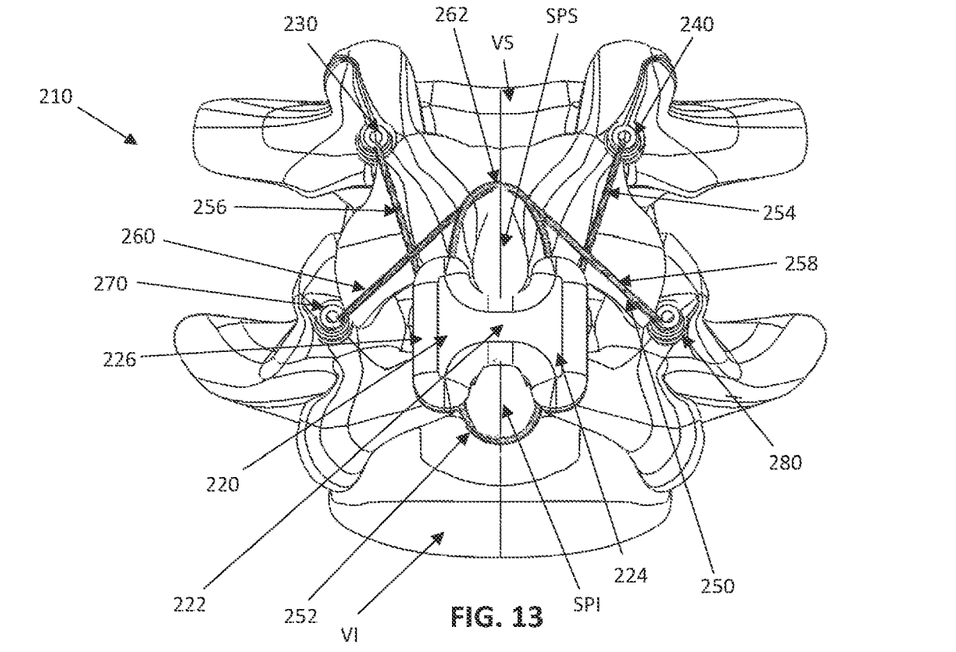
FIG. 13 is a posterior view of a third embodiment of an adjustable spinous process implant inserted between two adjacent vertebrae.
Figure 14:
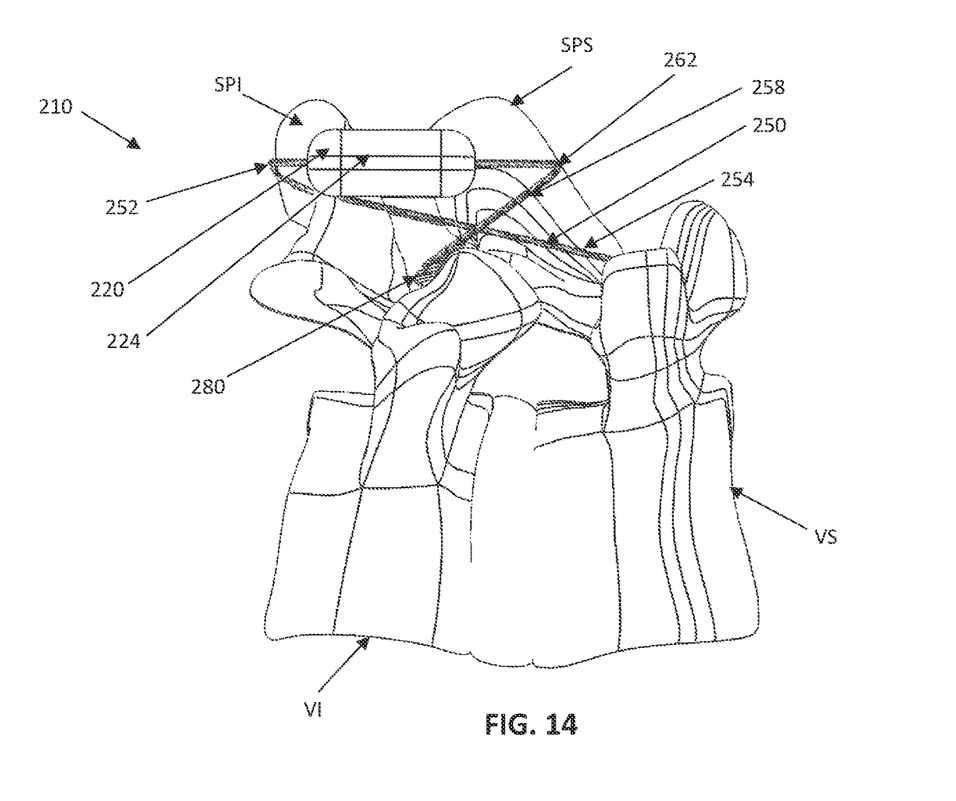
FIG. 14 is a lateral view of a third embodiment of an adjustable spinous process implant inserted between two adjacent vertebrae.
Figure 15:
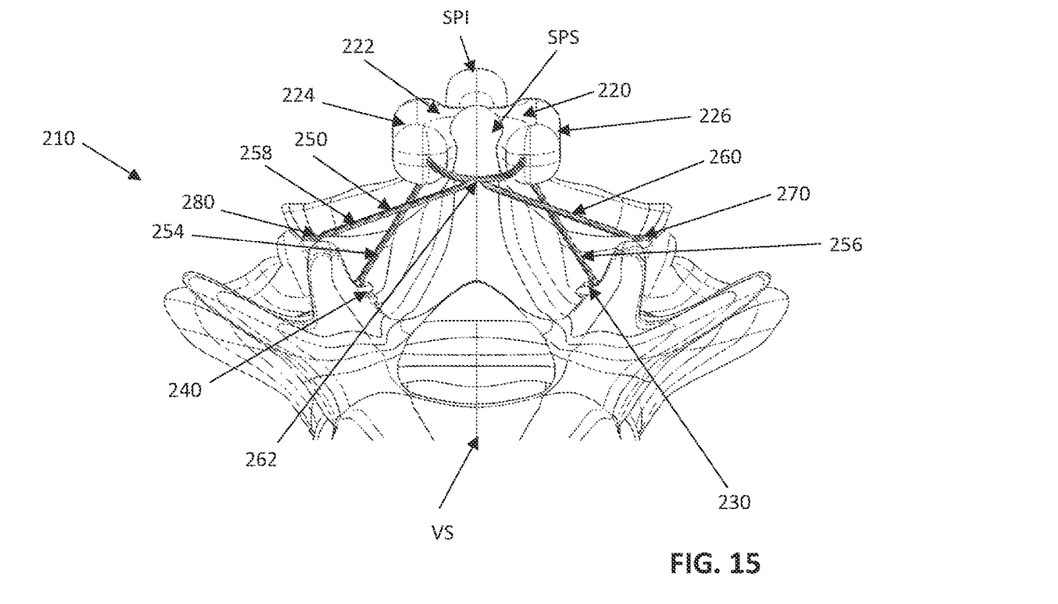
FIG. 15 is a superior view of a third embodiment of an adjustable spinous process implant inserted between two adjacent vertebrae.

As shown by at least FIG. 11 and FIG. 13, the central body 222 of the spacer 220 is designed to fit between the Inferior Spinous Process SPI and the Superior Spinous Process SPS of two adjacent vertebrae, where the Inferior Spinous Process SPI is on the Inferior Vertebra VI of the two vertebrae and the Superior Spinous Process SPS is on the Superior Vertebra VS of the two vertebrae. The right stabilizer 224 and left stabilizer 226 are configured to steady the spacer 220 between the Inferior Spinous Process SPI and the Superior Spinous Process SPS as the Inferior Vertebra VI and Superior Vertebra VS rotate with respect to one another. Additionally, the right stabilizer 224 and left stabilizer 226 cooperate to restrict the motion of the Inferior Spinous Process SPI and the Superior Spinous Process SPS relative to one another. As shown by at least FIGS. 13-15, both the right stabilizer 224 and left stabilizer 226 have portions that extend above and below the central body 222 of the spacer 220 to define a groove along both the lower and upper portions of the central body 222 that cradles the Inferior Spinous Process SPI and the Superior Spinous Process SPS, respectively. In the preferred embodiment, the spacer 220 may be made from flexible material such as a visco elastic polymer, or more rigid material such as polyether ether ketone (PEEK) or titanium. One of ordinary skill in the art would appreciate that there are numerous suitable and advantageous configurations for a spacer, including relative dimensions, size, and shapes, as well as different construction materials, depending on the intended use application, and embodiments of the present invention are contemplated for use with any such spacer configuration.

The third preferred embodiment of the adjustable spinous process implant 210 is further configured with a flexible member 250 that runs continuously through the spacer 220. The flexible member 250 may be one or more separate wires or cables integrated with or attached to the spacer 220. For example, each of the distal ends or loop(s) of the flexible member may be a separate wire or cable, with the separate wires or cables collectively comprising the flexible member. Furthermore, the wire(s) or cable(s) forming the flexible member 50, may pass straight through the stabilizers 224, 226 of the spacer 220, cross over in the central body 222, a combination thereof, or take any other path through the spacer 220 as necessary. In the various embodiments of the adjustable spinous implant 210, the distal ends and loop(s) of the flexible member 250 extend or protrude from various points along the spacer 220 in the given embodiment of the adjustable spinous implant 210. In some alternate embodiments of the flexible member 250, the flexible member does not run continuously through the spacer 220 and instead each distal end or loop, as described herein, is a separate component of the overall flexible member 250 that extends from a point on the spacer 220. In the third preferred embodiment, a right superior distal end 254 of the flexible member 250 protrudes from an inferior portion of the left stabilizer 226 of the spacer 220 and connects to a right superior anchor 240. Correspondingly, a left superior distal end 256 of the flexible member 250 protrudes from an inferior portion of the right stabilizer 224 of the spacer 220 and connects to a left superior anchor 230. Additionally, the inferior loop portion 252 of the flexible member 250 is formed by the right superior distal end 254 of the flexible member 250 crossing over with the left superior distal end 256 of the flexible member 250 below at the inferior portion of the spacer 220. The interior loop portion 252 of the flexible member 250 also wraps around the inferior edge of the Inferior Spinous Process SPI. The third embodiment of the adjustable spinous process implant 210 further comprises a right inferior distal end 258 of the flexible member 250 protrudes from a superior portion of the left stabilizer 226 of the spacer 220 and connects to a right inferior anchor 280. Correspondingly, a left inferior distal end 260 of the flexible member 250 protrudes from an superior portion of the right stabilizer 224 of the spacer 220 and connects to a left inferior anchor 270. Additionally, the superior loop portion 262 of the flexible member 250 is formed by the right inferior distal end 258 of the flexible member 250 crossing over with the left inferior distal end 260 of the flexible member 250 above at the superior portion of the spacer 220. The superior loop portion 262 of the flexible member 250 also wraps around the superior edge of the Superior Spinous Process SPS. In the third preferred embodiment, the flexible member 150 can be manufactured from any suitable material, including but not limited to, steel cable, polyethylene fibers, and suture wire.

In the third preferred embodiment, the left superior anchor 230 and right superior anchor 240 seat into the pedicle of the Superior Vertebrae VS, while the left inferior anchor 270 and right inferior anchor 280 seat into the pedicle of the Inferior Vertebrae VI. The proximal portion of the left superior anchor 230 attaches to the left superior distal end 256 of the flexible member 250 and the proximal portion of the right superior anchor 240 attaches to the right superior distal end 254 of the flexible member 250. Correspondingly, the proximal portion of the left inferior anchor 270 attaches to the left inferior distal end 260 of the flexible member 250 and the proximal portion of the right inferior anchor 280 attaches to the right inferior distal end 258 of the flexible member 250.

In the third preferred embodiment, the anchors 230, 240, 270, 280 have means by which the flexible member 250 can be tensioned within them. This enables a physician to tighten the flexible member 250 by drawing the distal ends 254, 256, 258, 260 into the respective anchors 230, 240, 270, 280 thereby tightening the inferior loop portion 252 around the Inferior Spinous Process SPI and tightening the superior loop portion 262 around the Superior Spinous Process SPS. The tightening of the various elements of the flexible member 250, collectively pull the vertebral bodies VI, VS towards one another, while also placing the spacer 220 under compression from the two Spinous Processes SPI, SPS. In the third preferred embodiment, the tensioning method can be a secondary screw mechanism within each of the anchors 230, 240, 270, 280 which pulls the distal ends 254, 256, 258, 260 of the flexible member 250 distally along each anchor 230, 240, 270, 280. Alternatively, the tensioning method can be similar to suture anchors whereby the distal ends 254, 256, 258, 260 of the flexible member 250 are looped inside of the respective anchors 230, 240, 270, 280 and the distal ends 254, 256, 258, 260 of the flexible member 250 can be pulled tight and tied off at the desired tightness. One of ordinary skill in the art would appreciate that there are numerous suitable and advantageous configurations for an anchor and a tensioning method therefor, and embodiments of the present invention are contemplated for use with any such anchor configuration and tensioning method.

Figure 16:
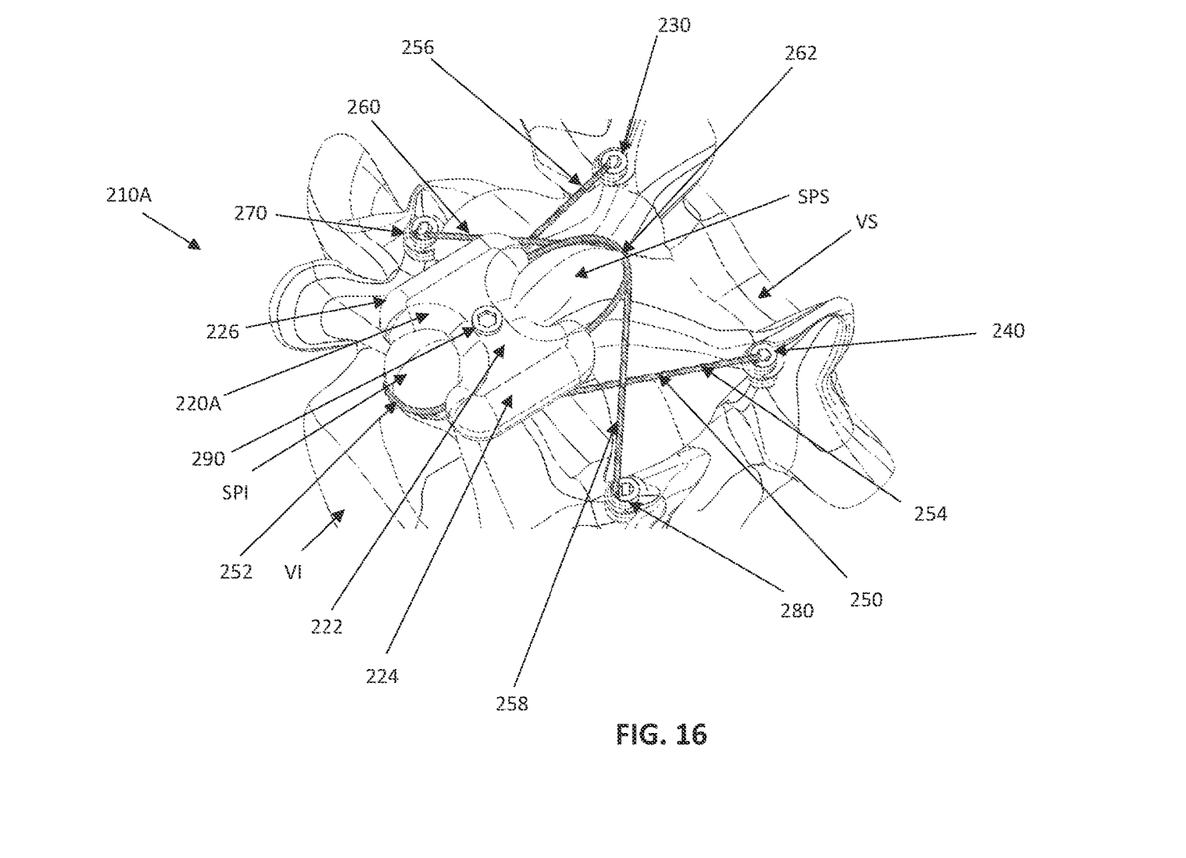
FIG. 16 is an isometric view of a fourth embodiment of an adjustable spinous process implant inserted between two adjacent vertebrae.

Turning now to FIG. 16, a fourth preferred embodiment of the adjustable spinous process implant 210A with an alternate preferred embodiment of the spacer 220A is shown. In the alternate preferred embodiment, the spacer 220A is modified and configured with a central turnbuckle 290. The turnbuckle 290 can be turned to tighten the flexible member 250. In this embodiment, the flexible member 250 may be comprised of two or more separate wires or cables that intersect at or otherwise attach to the turnbuckle 290. In some embodiments, each of the distal ends 254, 256, 258, 260 is a separate wire or cable component of the flexible member 250. Moreover, because the turnbuckle 290 is centrally located, the turnbuckle 290 can tighten all distal ends 254, 256, 258, 260 simultaneously. While FIG. 16 shows the alternate embodiment of the spacer 220A in the context of the third embodiment of the adjustable spinous process implant, the alternate preferred embodiment of the spacer 220A could be used in any embodiment of the adjustable spinous process implant.

Figure 17:
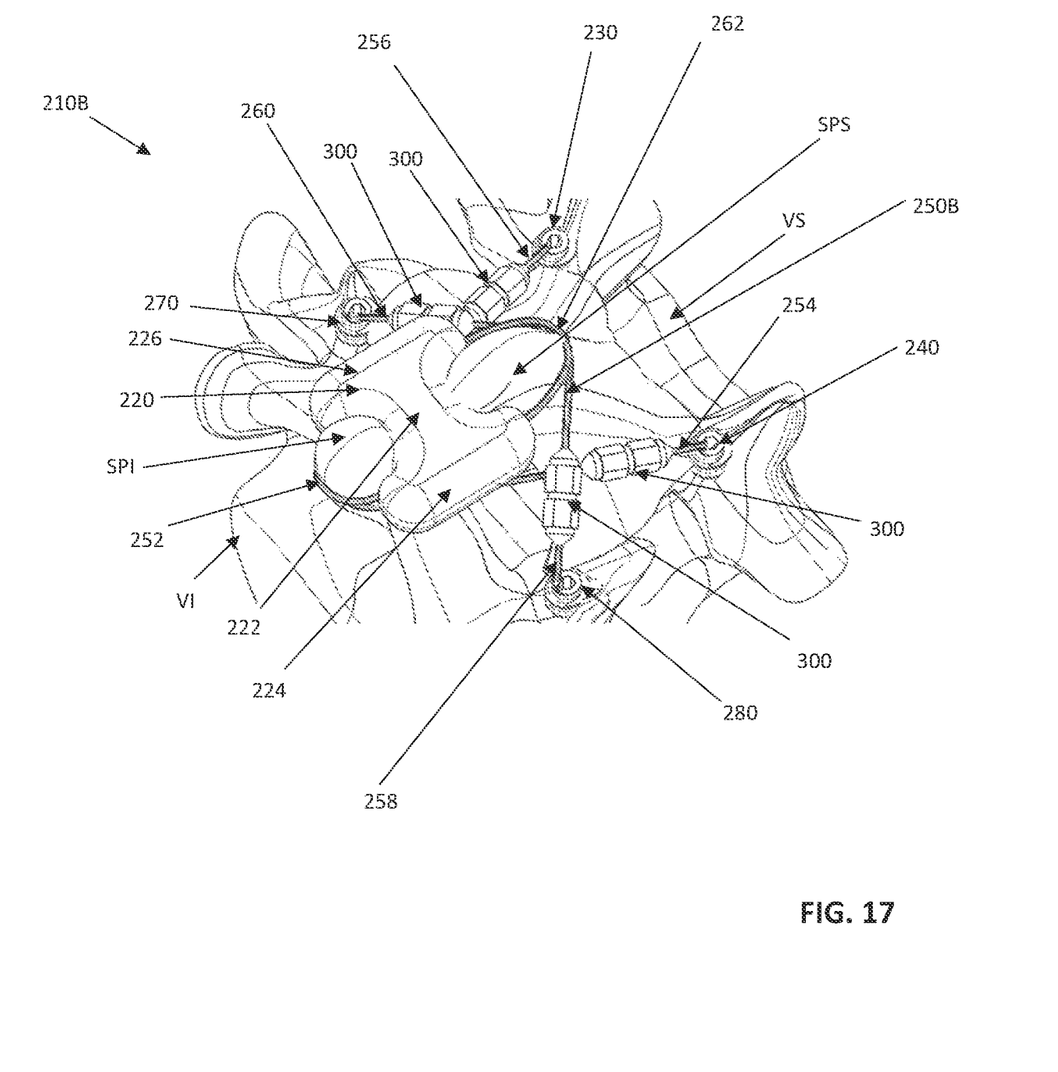
FIG. 17 is an isometric view of a fifth embodiment of an adjustable spinous process implant inserted between two adjacent vertebrae.

Turning now to FIG. 17, a fifth preferred embodiment of the adjustable spinous process implant 210B with an alternate preferred embodiment of the flexible member 250B is shown. In the alternate preferred embodiment, each of the distal ends 254, 256, 258, 260 of the flexible member 250B is modified and configured with a turnbuckle 300. The turnbuckle 300 on each of the distal ends 254, 256, 258, 260 can be turned to tighten the flexible member 250B. Furthermore, having a turnbuckle 300 on each of the distal ends 254, 256, 258, 260 allows for each distal end 254, 256, 258, 260 to be tightened individually. While FIG. 17 shows the alternate embodiment of the flexible member 250B in the context of the third embodiment of the adjustable spinous process implant, the alternate preferred embodiment of the spacer could be used in any embodiment of the adjustable spinous process implant.

Figure 18:
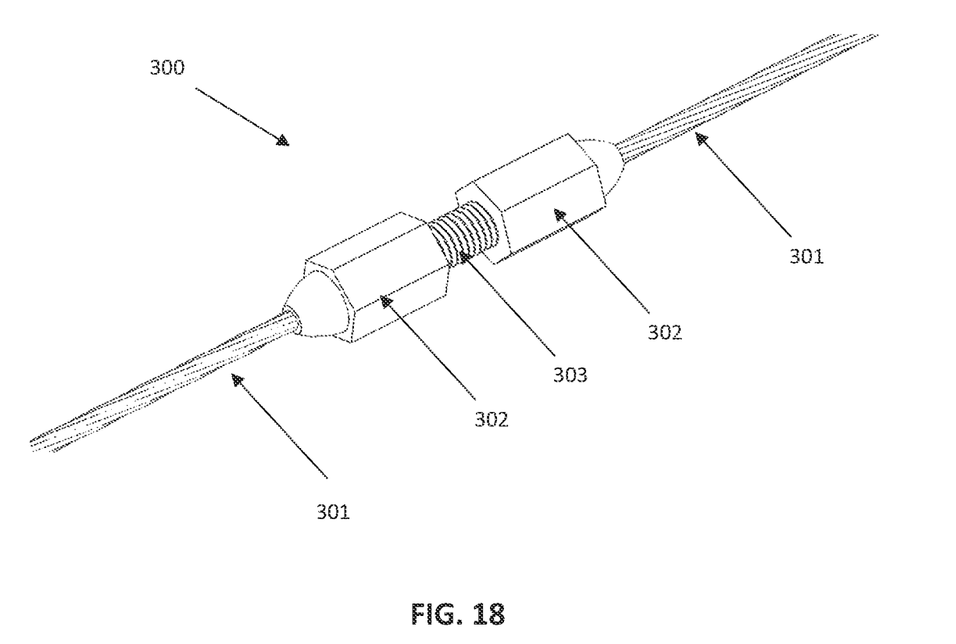
FIG. 18 is an isometric view of an embodiment of a turnbuckle configured as a cable tensioner on a flexible member.

Turning now to FIG. 18, an embodiment of a turnbuckle configured as a cable tensioner on a flexible member. In a preferred embodiment, a turnbuckle component 300 is configured to provide a mechanism to tighten the flexible member 301. The turnbuckle component 300 is attached in line with the flexible member 301 and comprised of two halves 302 that are joined by a threaded portion 303. Through this arrangement, tension can be increased or decreased in the flexible member 301 by tightening or loosening each of the turnbuckle halves 302 relative to the threaded portion 303 of the turnbuckle 300.

Figure 19:
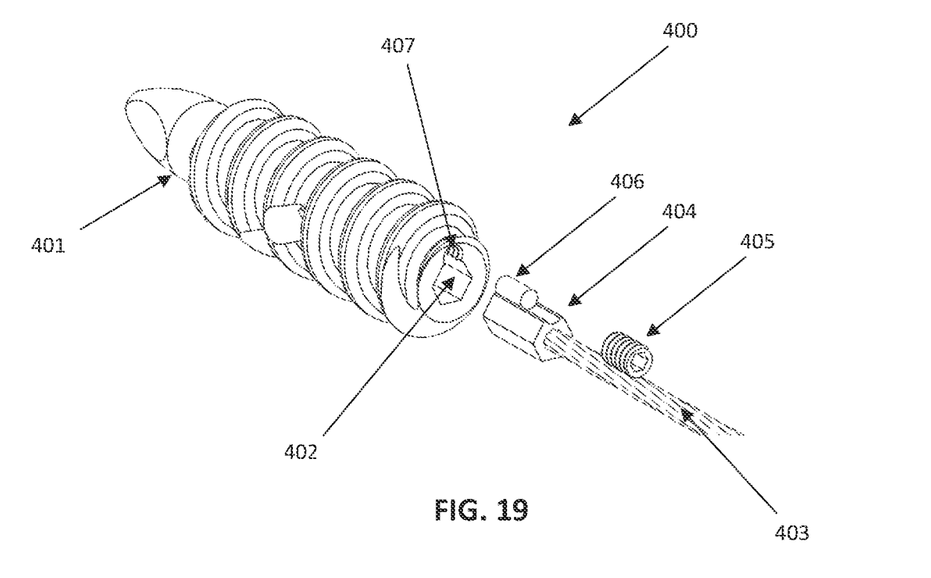
FIG. 19 is an isometric view of an anchor configured with a tensioning mechanism for a flexible member.

Turning now to FIG. 19, an anchor configured with a tensioning mechanism for a flexible member. In a preferred embodiment, the tensioning mechanism 400 is comprised of an anchor 401 formed with a shaft 402 configured to receive a fitting 404 that is attached to or formed on the distal end of the flexible member 403. With the fitting 404 first inserted into the shaft 402 formed in the anchor 401, a set screw 405 can be secured into a threaded portion 407 of the shaft 402. As the set screw 405 is driven deeper into the threaded portion 407 of the shaft 402, the set screw 405 abuts and pushes against the flange 406 of the fitting 404, thereby pushing the flexible member 403 deeper into the anchor 401 and increasing the tension on the flexible member 403 to generate a tighter fit between the anchor 401 and the implant.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, an apparatus described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

In the present disclosure, all embodiments where "comprising" is used may have as alternatives "consisting essentially of," or "consisting of" In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

The invention claimed is:

1. An adjustable spinous process implant comprising:
   a spacer;
   a central rotatable turnbuckle located within the spacer; and
   one or more flexible members extending from within the spacer, wherein at least two of the flexible members are operably connected with the central rotatable turnbuckle and the central rotatable turnbuckle is configured to simultaneously apply tension to all of the flexible members when the central rotatable turnbuckle is rotated in a first direction.

2. The implant of claim 1, wherein one or more of the flexible members terminates at a flexible member distal end.

3. The implant of claim 2, wherein each of the flexible members passes continuously through the spacer, beginning at one of the flexible member distal ends and terminating at another of the flexible member distal ends.

4. The implant of claim 2, wherein each of the flexible member distal ends forms a terminal segment of one of the flexible members.

5. The implant of claim 1, further comprising one or more loop portions formed from one or more of the one or more flexible members.

6. The implant of claim 1, wherein the spacer is formed with a central body connecting between a right stabilizer and a left stabilizer.

7. The implant of claim 6, wherein the central rotatable turnbuckle is configured in the central body.

8. The implant of claim 1, further comprising one or more anchors, each of the anchors configured to attach to one of the flexible member distal ends.

9. The implant of claim 8, wherein each of the anchors is configured with a tensioning mechanism comprising:
   a shaft formed in each of the anchors that is configured to receive a fitting on one of the flexible member distal ends; and
   a set screw configured to secure the fitting within the shaft and adjust tension in the flexible member distal end.

10. An adjustable spinous process implant comprising:
    a spacer;
    one or flexible members extending from the spacer, wherein at least one of the flexible members terminates at a distal end;
    one or more anchors each configured to receive and secure one of the flexible member distal ends; and
    one or more turnbuckles, wherein at least one of said turnbuckles is a rotatable turnbuckle that is located within the spacer and is configured to tighten the connection between the spacer and all of the anchors by simultaneously applying tension to all of flexible members when the rotatable turnbuckle is rotated in a first direction.

11. The implant of claim 10, wherein the spacer is formed with a central body connecting between a right stabilizer and a left stabilizer of the spacer.

12. The implant of claim 11, wherein the rotatable turnbuckle is configured in the central body.

13. The implant of claim 10, further comprising a fitting attached to at least one of the distal ends, wherein the anchor is formed with a shaft configured to receive the fitting.

14. An adjustable spinous process implant comprising:
a spacer;
one or flexible members extending from within the spacer, wherein at least one of the flexible members terminates at a distal end;
a fitting attached to at least one of the distal ends; and
one or more anchors each formed with a fitting shaft and a set screw shaft; wherein the fitting shaft is configured to receive the fitting of one of the distal ends and the set screw shaft is formed separately from the fitting shaft as a threaded groove extending into a side wall portion of the fitting shaft.

15. The implant of claim 14, further comprising a set screw that is received in the set screw shaft.

16. The implant of claim 15, wherein each of the fittings is formed with a set screw flange extending from a side wall of the fitting, the set screw flange being sized to fit within the set screw shaft.

17. The implant of claim 14, wherein a central axis of the fitting shaft is offset from a central axis of the set screw shaft.

* * * * *